(12) United States Patent
Liang et al.

(10) Patent No.: US 7,355,695 B2
(45) Date of Patent: Apr. 8, 2008

(54) WAVEFRONT CALIBRATION ANALYZER AND METHODS

(75) Inventors: Junzhong Liang, Fremont, CA (US);
Dimitri Chernyak, Sunnvale, CA (US);
Kingman Yee, San Jose, CA (US);
Seema Somani, Milpitas, CA (US);
Jeffrey J. Persoff, San Jose, CA (US);
Walter Huff, Scotts Valley, CA (US);
Charles Campbell, Berkeley, CA (US);
Charles R. Munnerlyn, San Jose, CA (US); Brian Bliven, San Jose, CA (US)

(73) Assignee: AMO Manufacturing USA, LLC, Santa Clara, CA (US)

(*) Notice: Subject to any disclaimer, the term of this patent is extended or adjusted under 35 U.S.C. 154(b) by 689 days.

(21) Appl. No.: 10/799,439

(22) Filed: Mar. 12, 2004

(65) Prior Publication Data

US 2004/0260275 A1  Dec. 23, 2004

Related U.S. Application Data (60) Provisional application No. 60/518,867, filed on Nov. 10, 2003, provisional application No. 60/461,739, filed on Apr. 9, 2003.

(51) Int. Cl.
*G01B 11/14* (2006.01)

(52) U.S. Cl. ............ 356/243.1; 606/5; 606/4; 606/10

(58) Field of Classification Search .. 356/243.1–243.8, 356/121–127; 606/4, 5, 10, 12
See application file for complete search history.

(56) References Cited

U.S. PATENT DOCUMENTS

| | | | |
|---|---|---|---|
| 4,669,466 A | 6/1987 | L'Esperance | |
| 5,460,627 A | 10/1995 | O'Donnell, Jr. | |
| 5,610,707 A | 3/1997 | Duncan et al. | |
| 5,772,656 A | 6/1998 | Klopotek | |
| 6,050,687 A | 4/2000 | Bille et al. | |
| 6,086,204 A | 7/2000 | Magnante | |
| 6,106,513 A | 8/2000 | McMillen et al. | |
| 6,116,737 A | 9/2000 | Kern | |
| 6,155,684 A | 12/2000 | Bille et al. | |
| 6,184,974 B1 | 2/2001 | Neal et al. | |
| 6,195,164 B1 | 2/2001 | Thompson et al. | |
| 6,234,631 B1 | 5/2001 | Sarver et al. | |
| 6,245,059 B1 | 6/2001 | Claphan | |
| 6,296,634 B1 | 10/2001 | McMillen et al. | |
| 6,338,559 B1 | 1/2002 | Williams | |

(Continued)

OTHER PUBLICATIONS

U.S. Appl. No. 11/755,194, filed May 30, 2007, Somani et al.

*Primary Examiner*—Hoa Q. Pham
(74) *Attorney, Agent, or Firm*—Townsend & Townsend & Crew LLP; Mark D. Barrish (57) ABSTRACT

A wavefront sensor enhances calibration of a laser ablation system, such as a laser eye surgery system, by measuring one or more characteristics of an ablated test surface. Typically, light is passed through the ablated test surface, and the light is analyzed to determine the test surface characteristics. In some embodiments, the ablated test surface is positioned along a treatment plane. In some embodiments, light is passed through a wavefront sensor, such as a Hartmann-Shack sensor, to convert the light into electrical signals. A processor then converts the electrical signals into data, such as surface maps showing high-order aberrations and/or artifacts on the test surface, refractive power measurements, shape measurements, and the like. Generated data may then be used to calibrate a laser surgery system.

44 Claims, 8 Drawing Sheets

U.S. PATENT DOCUMENTS

| | | |
|---|---|---|
| 6,364,873 B1 | 4/2002 | McMillen et al. |
| 6,419,671 B1 | 7/2002 | Lemberg |
| 6,460,997 B1 | 10/2002 | Frey et al. |
| 6,485,142 B1 | 11/2002 | Sheehy et al. |
| 6,559,934 B1 | 5/2003 | Yee et al. |
| 6,572,230 B2 | 6/2003 | Levine |
| 6,626,535 B2 | 9/2003 | Attmann |
| 6,626,924 B1 | 9/2003 | Klopotek |
| 6,637,884 B2 | 10/2003 | Martino |
| 6,666,855 B2 * | 12/2003 | Somani et al. ................. 606/5 |
| 6,673,062 B2 * | 1/2004 | Yee et al. ...................... 606/5 |
| 6,739,721 B2 | 5/2004 | Attmann |
| 6,793,654 B2 | 9/2004 | Lemberg |
| 6,846,310 B2 | 1/2005 | McMillen et al. |
| 7,001,375 B2 | 2/2006 | Yee et al. |
| 7,001,376 B2 | 2/2006 | Somani et al. |
| 7,040,759 B2 | 5/2006 | Chernyak et al. |
| 7,213,919 B2 | 5/2007 | Persoff |
| 7,238,177 B2 | 7/2007 | Somani et al. |
| 2001/0041884 A1 | 11/2001 | Frey et al. |
| 2002/0003606 A1 | 1/2002 | Pettit |
| 2002/0097376 A1 | 7/2002 | Applegate et al. |
| 2003/0007127 A1 | 1/2003 | Levine |
| 2003/0225399 A1 * | 12/2003 | Chernyak et al. ............... 606/5 |
| 2005/0024584 A1 | 5/2004 | Persoff |
| 2005/0096640 A1 | 5/2005 | Dai et al. |
| 2005/0131398 A1 | 6/2005 | Campbell et al. |
| 2005/0215986 A1 * | 9/2005 | Chernyak et al. ............... 606/5 |
| 2006/0084955 A1 | 4/2006 | Hindi et al. |
| 2006/0103839 A1 * | 5/2006 | Somani et al. ........... 356/241.1 |

* cited by examiner

FIG. 7B ized energy density of about 0.6 joule/cm² to about 1 joule/cm² 
WAVEFRONT CALIBRATION ANALYZER AND METHODS

CROSS REFERENCE TO RELATED APPLICATIONS

The present application claims the priority benefit of U.S. Provisional Patent Application Ser. Nos.: 60/461,739, filed Apr. 9, 2003, and 60/518,867, filed Nov. 10, 2003, the full disclosures of which are both hereby incorporated by reference.

BACKGROUND OF THE INVENTION

The present invention is directed generally to medical devices, methods and systems. More specifically, the invention is directed to methods, devices and systems for analyzing calibration of laser ablation systems.

Ultraviolet and infrared laser-based systems and methods are known for enabling ophthalmological surgery on the external surface of the cornea in order to correct vision defects. These procedures generally employ an ultraviolet or infrared laser to remove a microscopic layer of an anterior stromal tissue from the cornea to alter its refractive power. In ultraviolet laser ablation procedures, the radiation ablates corneal tissue in a photodecomposition that does not cause thermal damage to adjacent and underlying tissue. Molecules at the irradiated surface are broken into smaller volatile fragments without substantially heating the remaining substrate; the mechanism of the ablation is photochemical, i.e., the direct breaking of intermolecular bonds. The ablation penetrates into the stroma of the cornea to change its contour for various purposes, such as correcting myopia, hyperopia, and astigmatism.

In such laser-based systems and methods, the irradiated flux density and exposure time of the cornea to the laser radiation are controlled, to provide a surface sculpting of the cornea to achieve a desired surface change in the cornea. To that end, ablation algorithms have been developed that determine the approximate energy density that must be applied to remove a certain depth of tissue from the cornea. At ultraviolet wavelengths, for example, a cumulative energy density of about 0.6 joule/cm$^2$ to about 1 joule/cm$^2$ will typically ablate corneal tissue to a depth of about one micron when applied in a series of pulses of about 100 to 400 millijoules/cm$^2$. Accordingly, the ablation algorithms are tailored for each procedure depending on the amount and the shape of corneal tissue which will be removed to correct a particular individual's refractive error.

To properly use these laser ablation algorithms, the laser ablation system typically should be calibrated. Calibration of the laser system helps ensure removal of the intended shape and quantity of the corneal tissue so as to provide the desired shape and refractive power modification to the patient's cornea. In addition, it is usually desirable to test for acceptable levels of system performance. For example, such tests can help ensure that internal optics are aligned, that laser fluence is accurate, and the like.

Ablations of plastic test materials are often performed prior to excimer laser surgery to calibrate the energy density and ablation shape of the laser. During these tests, a lens is ablated into the test plastic, and the refractive power of the test lens is read by a standard lensometer. The reading from the lensometer is then entered back into the laser system so that the system can make appropriate calibration adjustments. The test lens may also be grossly evaluated under a magnifying glass, and test samples are sometimes sent to a laboratory for accurate evaluation to help determine beam homogeneity and quality.

Although known laser ablation calibration techniques are fairly effective, they still suffer from certain disadvantages. For example, delaying each surgery while obtaining accurate laboratory evaluations of a test lens may be impractical. Without such lab evaluations, when a user analyzes a test lens by merely examining the lens with the naked eye or using a conventional lensometer, it is almost impossible to detect high-order aberrations or artifacts on the test lens. Artifacts, generally, are localized/isolated ablation defects, often caused by inhomogeneity in the laser beam. Accurately estimating powers and shapes of the ablated test lens is also very subjective using only a conventional lensometer. On the other hand, requiring specialized test lens evaluation equipment, such as an interferometric surface profiler, at each site could add significantly to equipment costs and overall system complexity. Nonetheless, some information beyond an approximation of refractive power and a gross evaluation of the test lens would be helpful to improve the accuracy of regular calibrations, whether they are performed monthly, daily, or before each ablation procedure.

In light of the above, it would be desirable to provide improved methods, devices and systems for analyzing calibration of laser ablation systems. It would be particularly desirable if such improvements enhanced calibration accuracy without significantly increasing overall system costs and complexity. It would further be desirable if such improvements could provide quantifiable data which might be used in an automated calibration feedback and adjustment system. At least some of these objectives, will be achieved by the present invention.

BRIEF SUMMARY OF THE INVENTION

A wavefront sensor enhances calibration of a laser ablation system, such as a laser eye surgery system, by measuring one or more characteristics of an ablated test surface. Typically, light is passed through the ablated test surface and the light is analyzed to determine the test surface characteristics. In some embodiments, light is passed through a wavefront sensor, such as a Hartmann-Shack sensor, to convert the light into electrical signals. A processor then converts the electrical signals into data, such as surface maps showing aberrations and/or artifacts on the test surface, refractive power measurements, shape measurements, and the like. Generated data may then be used to calibrate a laser surgery system.

In some embodiments, the test surface is disposed along a treatment plane. By "treatment plane," it is meant any plane to which a laser may be directed from a laser system to perform an ablation procedure. Thus, when a test surface is disposed along a treatment plane, a subsequent treatment of an eye will typically be performed in the same plane where the test surface was positioned.

In one aspect of the invention, a method for analyzing calibration of a laser ablation system for performing an ablation procedure on an eye involves: selectively ablating a test surface with the laser system; directing light from a light source through the test surface; and analyzing the light with at least one calibration device, after the light has passed through the test surface, to determine a refractive power of the test surface and at least one additional ablation characteristic of the laser ablation system. In some embodiments, the test surface is disposed along a treatment plane, the treatment plane comprising a plane to which a laser is directed from the laser system to perform the ablation procedure, and the light is directed from the light source to the treatment plane through the test surface. In some embodiments, the light is analyzed with at least one calibration device. Optionally, the test surface may be fixedly positioned in the treatment plane during ablating, directing and analyzing. Such embodiments may optionally further include moving the test surface into the treatment plane before the ablating step. For example, the test surface may be coupled with a platform, and the platform may be moved to position the test surface into the treatment plane.

In some embodiments, the test surface is ablated into a lens. In some embodiments, selectively ablating comprises applying laser energy to the test surface to approximate at least one procedure, such as but not limited to astigmatic correction of a human eye, myopic correction of a human eye, hyperopic correction of a human eye, and a phototherapeutic flat. Some embodiments of the method further include moving at least part of the calibration device to a position in the treatment plane for analyzing the light. Such movement may be achieved, for example, by coupling at least a portion of the calibration device with a movable member, such as a pivot arm, a rotating arm, a linear slide, a frame pivot or the like.

The analyzing step may be accomplished via any suitable means. For example, in some embodiments, analyzing comprises using a wavefront sensor to analyze the light. The wavefront sensor, for example, may be selected from the group consisting of a Hartmann-Shack sensor, a Tscherning sensor, a ray tracing sensor, a shearing interferometer sensor, an amplitude grating sensor, and a pattern distortion measuring apparatus. Analyzing in many embodiments comprises determining at least one of a quality and a shape of the ablated test surface. Optionally, analyzing the quality of the ablated test surface may comprise detecting at least one aberration on the test surface. Also optionally, analyzing the quality of the ablated test surface may comprise detecting at least one high-order aberration or artifact on the test surface. In such embodiments, analyzing the quality may further comprise determining a height of the at least one high-order aberration artifact on the test surface. Some embodiments may further comprise generating at least one map of the test surface, the map showing a location of each of the high-order aberration(s) and/or artifact(s) on the test surface. Optionally, such a map may further show shapes of the high-order aberration(s) and/or artifact(s) on the test surface.

In some embodiments, the analyzing step generally comprises transforming the light into electrical signals and processing the electrical signals to determine refractive power and the at least one additional ablation characteristic. Transforming the light may comprise, for example, allowing the light to pass through a wavefront lens array and sensing the passed light with a light detection device. In some embodiments, for example, the light detection device comprises a charge coupled device. In some embodiments the method may also include adjusting at least one focusing lens disposed in a path between the test surface and the lens array to adjust the light before it passes through the lens array. Some embodiments may further include using the electrical signals to generate an image approximately representing the test surface. The image may include, for example, a surface map.

In some embodiments, the analyzing step includes measuring wavefront data pertaining to the light and using a reconstruction algorithm to generate a surface map of the test surface. Using the reconstruction algorithm, in some embodiments, may comprise using a Zernike reconstruction algorithm or a Fourier reconstruction algorithm. Some embodiments of the method further include adjusting the laser ablation system based on the refractive power and the at least one additional ablation characteristic determined during the analyzing step. The at least one ablation characteristic may include, for example, at least one of a quality and a shape of the ablated test surface.

In another aspect of the present invention, a calibration apparatus for use with a laser ablation system, the laser ablation system capable of reshaping a surface by selective laser ablation of the surface, includes: a selectively laser ablatable test surface; a light detection assembly; a light source for passing light to the treatment plane, towards the light detection assembly; and a processor coupled with the light detection assembly for analyzing the detected light to determine a refractive power of the test surface and at least one additional ablation characteristic of the laser ablation system. In some embodiments, the ablatable test surface is positionable along a treatment plane, the treatment plane comprising a plane to which a laser is directed from the laser system to perform a reshaping procedure. In such embodiments, the light source is configured to pass light to the treatment plane, through the ablated test surface, towards the light detection assembly. In some embodiments, the test surface is fixedly positioned along the treatment plane while the laser ablatable test surface is ablated and light is passed through the test surface from the light source. For example, some embodiments of the apparatus may further include a movable platform to which the test surface is coupled, wherein the platform is movable to position the test surface along the treatment plane.

In some embodiments, the ablatable test surface comprises a lens. Also in some embodiments, the light detection assembly comprises a wavefront sensor. The wavefront sensor may include, for example, a Hartmann-Shack sensor, a Tscherning sensor, a ray tracing sensor, a shearing interferometer sensor, an amplitude grating sensor, a pattern distortion measuring apparatus or the like. In other embodiments, the light detection assembly may comprise a sensor such as a shearing interferometer sensor, an amplitude grating sensor, or a pattern distortion measuring apparatus.

In some embodiments, the light detection assembly comprises a charge coupled device for transforming the light into electrical signals. Sometimes the processor may be coupled with the charge coupled device for analyzing the electrical signals to determine the refractive power and the at least one additional ablation characteristic. Optionally, the processor may be further coupled with the laser ablation system for calibrating the laser ablation system based on the analysis of the electrical signals. In some embodiments, the processor includes means for applying a Zernike reconstruction algorithm or a Fourier reconstruction algorithm to derive at least one surface map of the test surface from wavefront data measured by the light detection assembly. In some embodiments, the apparatus further comprises at least one adjustment lens disposed between the light source and the light detection assembly for adjusting at least one characteristic of the light.

In some embodiments, the at least one additional ablation characteristic comprises at least one of a quality and a shape of the ablated test surface. For example, the quality may comprise at least one of an aberration and an artifact in the ablated test surface. Optionally, the processor may generate at least one image of the ablated test surface, the at least one image showing the at least one aberration or artifact. In some embodiments, the at least one image comprises at least one surface map of the test surface. Optionally, the processor may generate at least one measurement of at least one aberration or artifact. In some embodiments, the processor is coupled with the laser ablation system. Furthermore, in some embodiments the processor automatically calibrates the laser ablation system, based on at least one of the refractive power and the at least one additional ablation characteristic.

DETAILED DESCRIPTION OF THE INVENTION

The present invention generally provides improved methods, devices and systems for analyzing calibration of laser ablation systems. In particular, the invention relates to methods, devices and systems for measuring the refractive power and at least one other ablation characteristic of a laser test ablation on a test surface. The other characteristic may include, for example, a shape or quality of the test surface, the presence, locations and/or sizes of aberrations and artifacts on the test surface, and the like. Devices and methods of the present invention provide for measuring such characteristics at the treatment plane. By "treatment plane," it is meant a plane along which a laser treatment is to be performed on a human eye. A laser calibration device may be positioned along a treatment plane by any suitable means, such as by coupling the device with a movable member, such as a pivot arm, a jointed arm, a rotating arm, a linear slide or the like.

In some embodiments, a laser wavefront sensor may generate one or more surface maps of an ablated test surface and/or may automatically calibrate a laser ablation system. The present invention may be used with any suitable laser ablation system in any suitable setting, but is particularly useful for enhancing calibration of excimer lasers used during laser ablation procedures of the eye, such as photorefractive keratotomy (PRK), phototherapeutic keratectomy (PTK), laser in situ keratomileusis (LASIK) and the like. In various embodiments, devices of the present invention may be easily adapted for use with existing laser systems, may be incorporated into new laser systems, may comprise standalone devices compatible with existing or new systems, and/or the like.

Typically, methods of the invention involve: selectively ablating a test surface with the laser system; directing light from a light source along a treatment plane through the test surface, wherein the treatment plane comprises a plane along which a laser is directed from the laser system to perform the ablation procedure; and analyzing the light with at least one calibration device disposed along the treatment plane, after the light has passed through the test surface, to determine a refractive power of the test surface and at least one additional ablation characteristic of the laser ablation system. In some embodiments, for example, devices and methods of the invention may be used to measure refractive power as well as shape and/or quality of the laser test ablation on the test surface. In some embodiments, the analysis of the light that has passed through a test surface is achieved using a wavefront measurement device, such as a Hartmann-Shack wavefront sensor. In other embodiments, however, as described further below, alternative measurement devices may be used for analyzing light from a test surface.

The term "test surface" is used in this application to refer to any test material, test lens or the like that may be ablated by a laser ablation system in a testing capacity. In many embodiments, such a test surface comprises a plastic or other material which is ablated by a laser ablation device to form a test lens. The ablation device typically ablates the test surface just as it would ablate a portion of an eye during a laser ablation procedure on the eye. The test surface can then be used to determine the calibration of the laser, using the devices and methods of the present invention.

Figure 1:
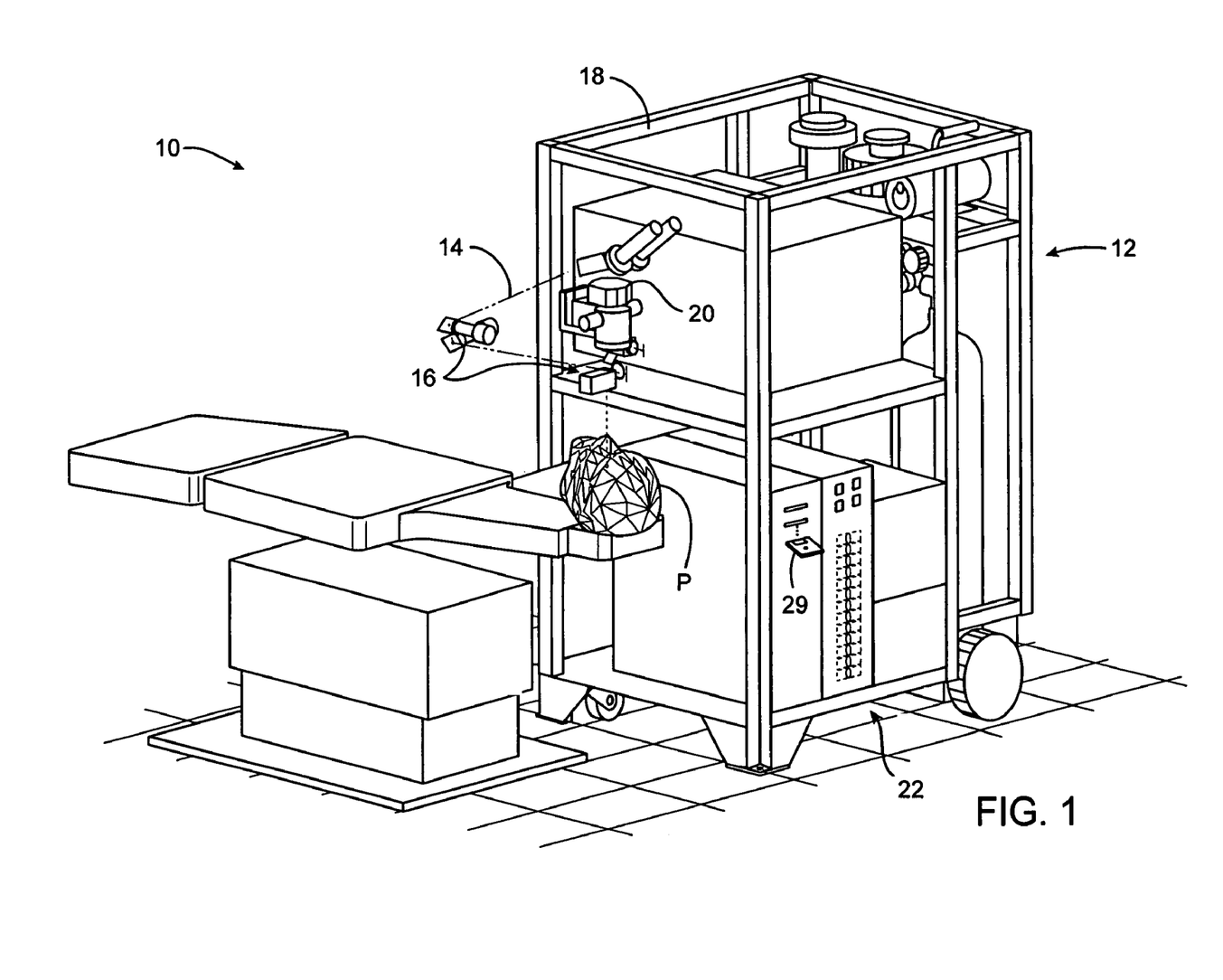
FIG. 1 is a perspective view of a laser eye surgery system.

Referring now to FIG. 1, a laser eye surgery system 10 which may make use of devices and/or methods of the present invention suitably includes a laser 12 that produces a laser beam 14. Laser 12 is optically coupled to laser delivery optics 16, which directs laser beam 14 to an eye of patient P. A delivery optics support structure (not shown here for clarity) extends from a frame 18 supporting laser 12. A microscope 20 is mounted on the delivery optics support structure, the microscope often being used to image a cornea of an eye. A similar laser eye surgery system 10 is described in U.S. patent application Ser. No. 09/960,163, Publication No. US 2002/0097375, the entire disclosure of which is hereby incorporated by reference.

Laser 12 generally comprises an excimer laser, ideally comprising an argon-fluorine laser producing pulses of laser light having a wavelength of approximately 193 nm. Laser 12 will preferably be designed to provide a feedback stabilized fluence at the patient's eye, delivered via delivery optics 16. The present invention may also be useful with alternative sources of ultraviolet or infrared radiation, particularly those adapted to controllably ablate the corneal tissue without causing significant damage to adjacent and/or underlying tissues of the eye. Such sources include, but are not limited to, solid state lasers and other devices which can generate energy in the ultraviolet wavelength between about 185 and 215 nm and/or those which utilize frequency-multiplying techniques. Hence, although an excimer laser is the illustrative source of an ablating beam, other lasers may be used in the present invention.

Laser 12 and delivery optics 16 will generally direct laser beam 14 to the eye of patient P under the direction of a processor 22. Processor 22 will generally selectively adjust laser beam 14 to expose portions of the cornea to the pulses of laser energy so as to effect a predetermined sculpting of the cornea and alter the refractive characteristics of the eye.

In many embodiments, both laser 12 and the laser delivery optical system 16 will be under computer control of processor 22 to effect the desired laser sculpting process, with the processor ideally altering the ablation procedure in response to inputs from an optical feedback system. The feedback will preferably be input into processor 22 from an automated image analysis system, or may be manually input into the processor by a system operator using an input device in response to a visual inspection of analysis images provided by the optical feedback system. Processor 22 will often continue and/or terminate a sculpting treatment in response to the feedback, and may optionally also modify the planned sculpting based at least in part on the feedback.

Laser beam 14 may be adjusted to produce the desired sculpting using a variety of alternative mechanisms. The laser beam 14 may be selectively limited using one or more variable apertures. An exemplary variable aperture system having a variable iris and a variable width slit is described in U.S. Pat. No. 5,713,892, the full disclosure of which is incorporated herein by reference. The laser beam may also be tailored by varying the size and offset of the laser spot from an axis of the eye, as described in U.S. Pat. No. 5,683,379, and as also described in co-pending U.S. patent application Ser. Nos. 08/968,380, filed Nov. 12, 1997; and 09/274,999 filed Mar. 22, 1999, the full disclosures of which are incorporated herein by reference.

Still further alternatives are possible, including scanning of the laser beam over the surface of the eye and controlling the number of pulses and/or dwell time at each location, as described, for example, by U.S. Pat. No. 4,665,913 (the full disclosure of which is incorporated herein by reference) and as demonstrated by other scanning laser systems such as the LaserScan LSX® laser by LaserSight® Technologies, Inc., the Allegretto® Laser by Wavelight, LADARVision® by Alcon, and the 217C and 217A excimer lasers by Bausch & Lomb; using masks in the optical path of laser beam 14 which ablate to vary the profile of the beam incident on the cornea, as described in U.S. patent application Ser. No. 08/468,898, filed Jun. 6, 1995 (the full disclosure of which is incorporated herein by reference); hybrid profile-scanning systems in which a variable size beam (typically controlled by a variable width slit and/or variable diameter iris diaphragm) is scanned across the cornea; or the like. The computer programs and control methodology for these laser pattern tailoring techniques are well described in the patent literature.

Additional components and subsystems may be included with laser system 10. For example, spatial and/or temporal integrators may be included to control the distribution of energy within the laser beam, as described in U.S. Pat. No. 5,646,791, the disclosure of which is incorporated herein by reference. An ablation effluent evacuator/filter, and other ancillary components of the laser surgery system which are not necessary to an understanding of the invention, need not be described in detail for an understanding of the present invention.

As mentioned above, laser system 10 will generally include a computer or programmable processor 22. Processor 22 may comprise (or interface with) a conventional PC system including the standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying steps or programming instructions for any of the methods of the present invention. Tangible storage media 29 may take the form of a floppy disk, an optical disk, a data tape, a non-volatile memory, or the like, and the processor 22 will include the memory boards and other standard components of modern computer systems for storing and executing this code.

Figure 2:
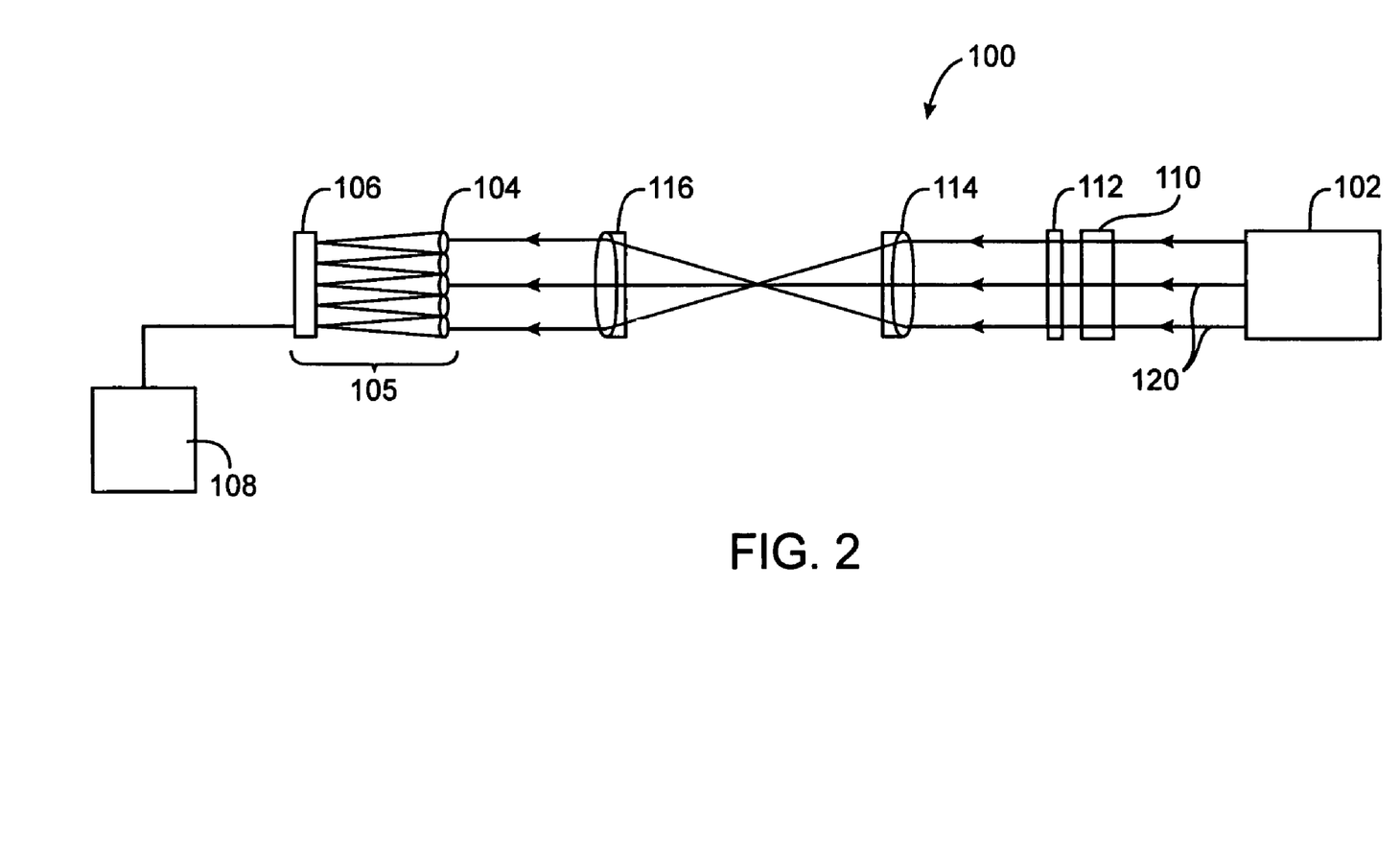
FIG. 2 is a side view of a wavefront sensor device according to an embodiment of the present invention.

Referring now to FIG. 2, a wavefront sensor 100 for analyzing calibration of a laser ablation system using a Hartmann-Shack wavefront sensor is schematically illustrated according to an embodiment of the present invention. In various embodiments, wavefront sensor 100 may either be incorporated into a laser ablation system such as the one described above, may be coupled with such a laser ablation system, or may comprise a stand-alone calibration system. In some embodiments, wavefront sensor 100 may be used merely to analyze calibration, while in other embodiments analyzer 100 may also be used to calibrate a laser ablation system. In some embodiments, analyzer 100 calibrates a laser ablation system automatically. As mentioned above, wavefront sensor 100 may be positioned so as to analyze calibration of a laser ablation system in a treatment plane. As such, wavefront sensor 100 may be either wholly or partially positioned in the treatment plane and may be fixedly or movably positioned in the treatment plane. In some embodiments, all or part of wavefront sensor 100 may be coupled with a moveable member, such as a movable arm, linear sliding track or the like to provide movable positioning in the treatment plane.

Generally, wavefront sensor 100 includes a light source 102, a selectively laser ablatable test surface 110, a light detection assembly 105, and a processor 108. In some embodiments, light detection assembly 105 comprises a lenslet array 104 and a light sensor device 106, while in other embodiments light detection assembly 105 comprises alternative and/or additional components. As described further below, in some embodiments light detection assembly comprises a wavefront sensor, such as a Hartmann-Shack sensor, a Tscherning sensor, a ray tracing sensor, a shearing interferometer sensor, an amplitude grating sensor, or a pattern distortion measuring apparatus. Other embodiments, however, may include any other suitable light detection assemblies. Optionally, various embodiments of wavefront sensor 100 may also include one or more filters 112, such as a bandpass filter, adjustment lenses 114, 116, one or more reflective surfaces such as mirrors (not shown), additional optical components (not shown), and/or any other suitable components positioned at suitable locations along the device.

Light source 102, which may be powered via an internal or external power supply (not shown), generally provides light 120 directed through test surface 110. In some embodiments, light 120 may pass through a reference structure or other component(s) before passing through test surface 110, but such a reference structure is not required. Light rays 120 then pass through any additional, optional optics, such as bandpass filter 112 and lenses 114, 116, before passing through to light detection assembly 105. Optional adjustment lenses 114, 116, for example, may be used to focus light 120 on lens array 104, adjust the width of the light pattern, and/or the like. In some embodiments, light source 102 may be offset relative to one or more other components of wavefront sensor 100, and one or more mirrors or other reflective surfaces may be used to direct light 120 in a desired path. Thus, although wavefront sensor 100 is shown as comprising generally a straight line in FIG. 2, any suitable configuration is contemplated within the scope of the invention.

Wavefront technology is one way that laser ablation eye surgical systems may track and measure optical characteristics of a patient's eye. Wavefront measurement of the eye typically creates a high order aberration map that permits assessment of aberrations throughout the optical pathway of the eye, for example both internal aberrations and aberrations on the corneal surface. The aberration information can then be used to compute a custom ablation pattern for allowing a surgical laser system to correct the complex aberrations in and on the patient's eye. In various embodiments of the present invention, wavefront technology is used to measure optical characteristics of test surface 110, rather than of a patient's eye.

One exemplary wavefront technology system is the VISX WaveScan® system, which uses Hartmann-Shack wavefront sensors that can quantify aberrations throughout the entire optical system of the patient's eye, including sphero-cylindrical errors, coma, and a host of other high-order aberrations. The aberrations in and on the patient's eye can be displayed to the surgeon in the form of an aberration map. Rather than passing light into a patient's eye, devices and methods of the present invention involve passing light through test surface 110 and then through light detection assembly 105, one embodiment of which is a Hartmann-Shack wavefront sensor.

Light sensor device 106 generally transforms light 120 that contacts it into electrical signals. As such, light sensor device 106 may comprise any suitable device for converting or transforming light 120 into electrical signals. In some embodiments, for example, light sensor device 106 may comprise a charge-coupled device (CCD), which converts the light 120 that contacts it into digital image signals, so that the image information can be analyzed by processor 108.

Processor 108 typically comprises hardware, software, and/or firmware arranged to calculate one or more optical characteristics of the image of light that contacts light sensor device 106. Processor 108 will often determine optical quality, optionally by measuring the smallest features or spatial frequencies which are accurately reproduced in the image that contacts the light sensor device 106. Processor 108 may also determine refractive power and/or shape of test surface 110. More complex analysis may also be provided. Processor 108 may be described as being an optical transfer function calculation device, a modulation transfer function calculation device, or the like, depending on which quality measurement is used within the system.

After light 120 is converted into electrical signals by light sensor device 106, the electrical signals are typically processed to provide data. The data may then be used, for example, to calibrate the laser ablation system used to ablate test surface 110. Processor 108 may comprise any of a number of various components, such as an image grabber, a switch, a computer, a display, and/or any other suitable components or combinations. In some various embodiments, processor 108 generates data such as but not limited to ablation depths along the surface of test surface 110, ablation shapes, presence of aberrations such as high order aberrations, presence of artifacts, powers of test surfaces, overall shapes of test surfaces (cylindrical, spherical, etc.), heights or depths of surface aberrations or artifacts, and/or the like. Such data may be provided by processor 108 in any suitable form, such as in the form of a two-dimensional surface map, a three-dimensional surface map, a chart, a table, a graph and/or any other readout on a digital display. Surface maps of test surface 110 may show, for example, ablation patterns, shapes and depths of high-order aberrations, artifact shapes and depths, locations of aberrations and artifacts, and/or the like. In some embodiments, such data may be input directly into a calibration system of a laser ablation system to enable a calibration based on the data derived from processor 108. Generally, processor 108 may be used to perform any processing function of electrical signals from light sensor device 106 into data.

Figure 2A:
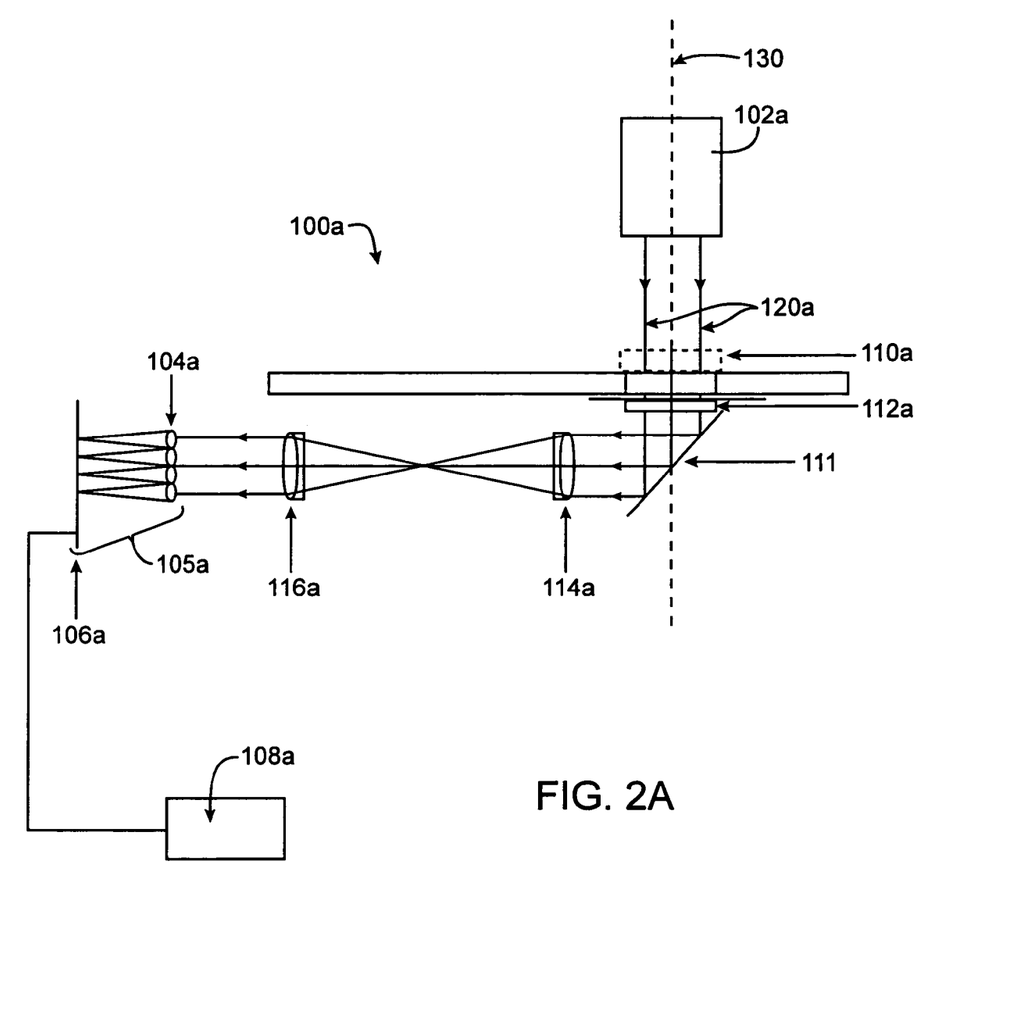
FIG. 2A is a side view of a wavefront sensor device with a test surface positioned along a treatment plane according to an embodiment of the present invention.

Referring now to FIG. 2A, in a preferred embodiment of the invention a wavefront sensor 100a includes components similar to those described above, including a light source 102a for providing light 120a, a test surface 110a, a band-pass filter 112a, lenses 114a and 116a, a light detection assembly 105a including a lenslet array 104a and a light sensor device 106a, and a processor 108a. This embodiment also includes one or more mirrors 111 to reflect light 120a. In this embodiment, test surface 110a is positioned in a treatment plane 130. As described above, a "treatment plane" is defined as any plane to which a laser may be directed from a laser system to perform an ablation procedure. Thus, in FIG. 2A, light 120a is directed along treatment plane 130 to pass through test surface 110a, which is located along treatment plane 130, and subsequently to pass through the other components of wavefront sensor 100a. In other embodiments, light may be passed to a treatment plane, but not along the plane, to pass through the test surface. As has been described above, disposing test surface 110a in treatment plane 130 may provide a number of advantages in preparing and performing a laser ablation procedure.

Figure 3:
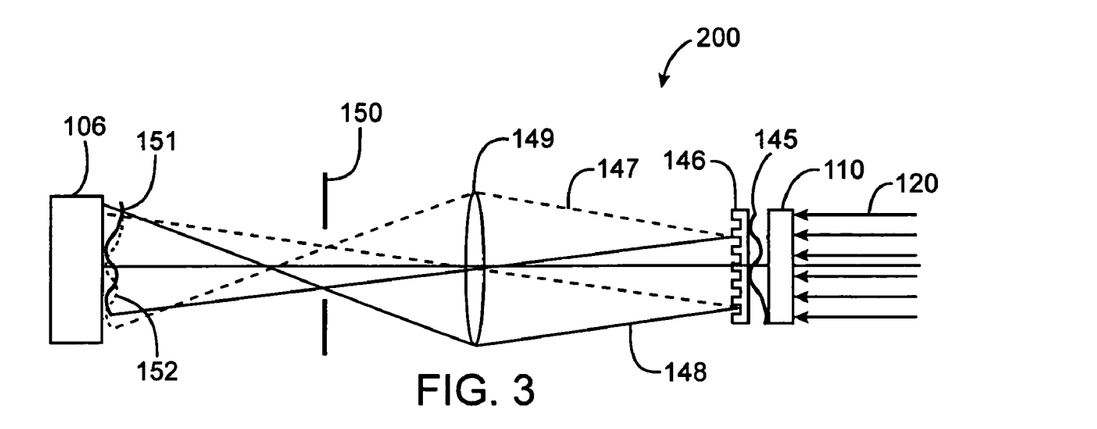
FIG. 3 is a side view of a wavefront sensor device according to another embodiment of the present invention.

With reference now to FIG. 3, various embodiments of a wavefront sensor may be used that differ from the Hartmann-Shack embodiment described above yet provide analogous wavefront information. As shown in FIG. 3, for example, one embodiment of a wavefront sensor may comprise a shearing interferometer device 200. Shearing interferometer 200 suitably includes a half-wave phase plate array 146, an imaging lens 149 and an aperture stop 150 arranged between test surface 110 and light sensor device 106. In one embodiment, phase plate array 146 is positioned relatively close to test surface 110 so that an aberrated wavefront 145 created by light 120 passing through test surface 110 has little distance to propagate before it is intercepted by phase plate array 146.

Figure 3A:
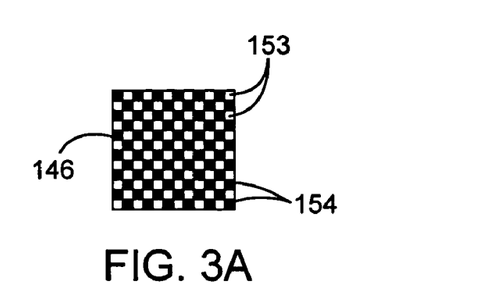
FIG. 3A is a frontal view of a phase plate array as used in the embodiment of the wavefront sensor device shown in FIG. 3.

In one embodiment, as shown in FIG. 3A, phase plate array 146 may comprise a checkerboard pattern of elements, with uncolored square elements 153 optically thicker than colored square elements 154 by one-half a wavelength of light 120 provided by light source (not shown). Phase array 146 thus acts as a diffraction grating, dividing the aberrated wavefront 145 into odd diffraction orders but creating no even orders, or zero order. The +1 and −1 orders so created are shown as light beams 147 (dashed lines) and 148 (solid lines). These beams 147, 148, each carrying aberration information, intersect and are focused by lens 149. Aperture 150 is positioned in the focal plane of lens 149, where beams 147, 148 come to focus. In this plane each order becomes a focused spot, displaced from the other orders by virtue of the fact that each order passes into lens 149 at a different angle in a specific direction of diffraction.

Figure 3B:
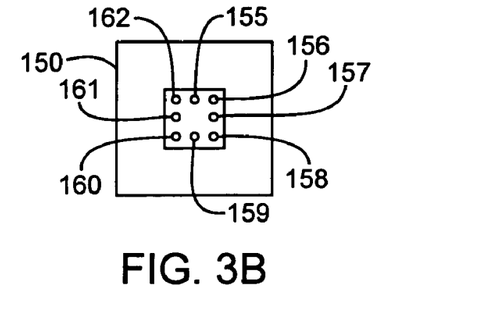
FIG. 3B is a frontal view of an aperture as used in the embodiment of the wavefront sensor device shown in FIG. 3.

In one embodiment, as shown in FIG. 3B, aperture 150 has clear areas at the locations of the first order diffraction spots but is otherwise opaque. Hence only the first order beams, shown by the diffraction focal points 155, 156, 157, 158, 159, 160, 161 and 162, pass through the aperture. These spots represent the x+1 and −1 orders, the y+1 and −1 orders, and the x,y mixed first orders. All other orders are blocked.

The first order beams 147, 148 pass on to light sensor device 106, typically a charge coupled image sensor, which lies in the plane where lens 149 creates images in each diffracted beam of aberrated wavefront 145. These images, 151 and 152, are displaced or sheared with respect to one another and they interfere to produce a fringe pattern known as a shearing interferogram. From such a shearing interferogram, the gradient or slope information of the original wavefront may be obtained via image processing, thus providing information analogous to that obtained from a Hartmann-Shack wavefront sensor.

Figure 4:
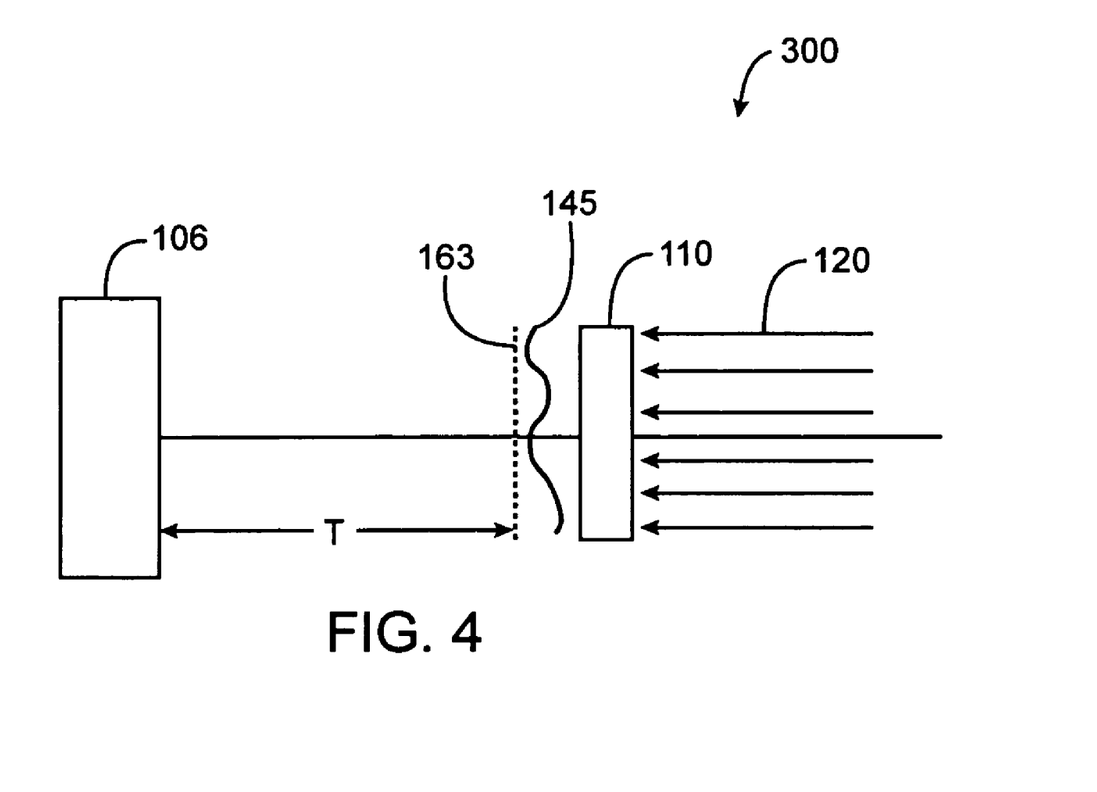
FIG. 4 is a side view of a wavefront sensor device according to another embodiment of the present invention.
Figure 4A:
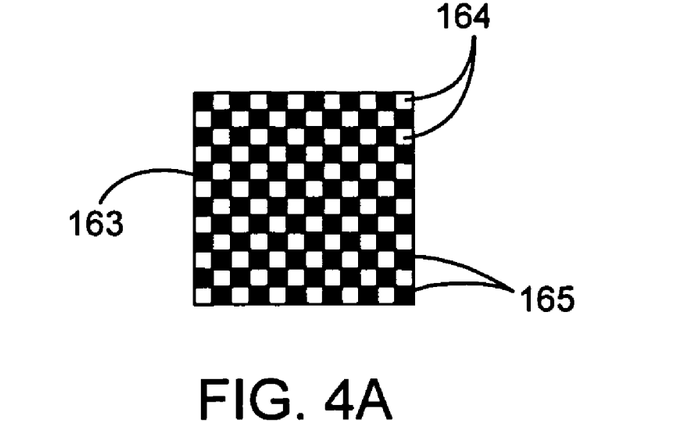
FIG. 4A is a frontal view of a crossed grid sinusoidal amplitude grating as used in the embodiment of the wavefront sensor device shown in FIG. 4.

Referring now to FIG. 4, in another embodiment of a wavefront sensor, wavefront gradient measurement may be provided via a grating analyzer 300. Grating analyzer 300 generally includes a crossed grid sinusoidal amplitude grating 163 located at distance T from light sensor device 106, typically a charge coupled array. As aberrrated wavefront 145 passes through grating 163, diffraction takes place in the Talbot plane, located at distance T from grating 163 and in the plane of light sensor device 106, a diffraction pattern is formed. The Fourier transform of this diffraction pattern is taken and from it the wavefront gradient information may be extracted. FIG. 4A shows a frontal view of crossed grid sinusoidal amplitude grating 163. At the center of clear squares 164, the transmission fraction of the grating is 1.0. This transmission amplitude decreases in a sinusoidal fashion until at the center of gray squares 165 the transmission fraction of the grating is 0.0.

Figure 5:
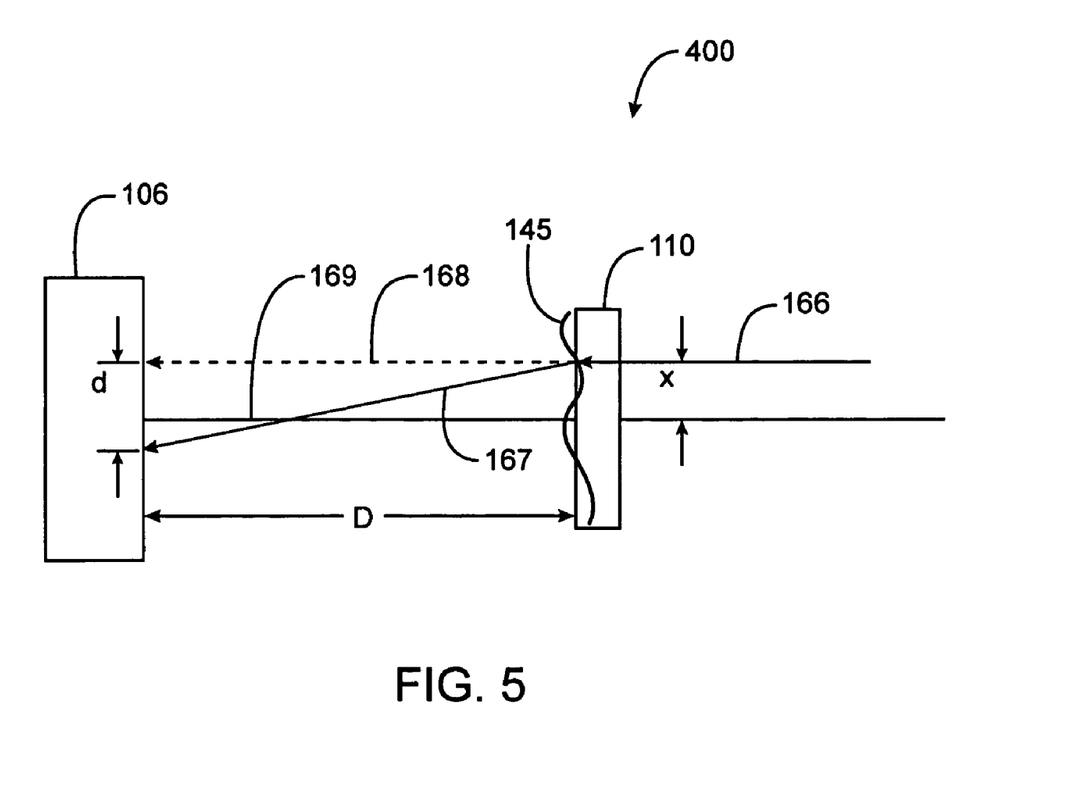
FIG. 5 is a side view of a wavefront sensor device according to another embodiment of the present invention.

As mentioned above, and with reference now to FIG. 5, yet another embodiment of a wavefront sensor may include a ray tracing sensor device 400 capable of measuring a wavefront gradient. In this type of sensor the wide collimated light beam 120 of the Hartmann-Shack sensor is replaced with a thin beam of light 166 that may be sequentially moved parallel to itself so that it sequentially samples ablated test surface 110 at different, known locations x. At each sampled location beam 166 is deflected to a path 167 and strikes light sensor device 106, located at distance D from test surface 110. If beam 166 had not been deflected, it would have followed an alternate path 168 and intersected sensor device 106 a distance d from the position that the actual path 167 strikes the sensor. The value d is measured by light sensor device 106. The ratio d/D is the tangent of the deflection angle 169. This ratio is the slope of aberrated wavefront 145 at location x. From a series of such measurements at different x locations over the surface of the ablated test surface, the wavefront may be reconstructed. Optionally, any number of beams passed through test object 110 at a number of known locations may be used to measure the gradient at multiple locations simultaneously.

Figure 6:
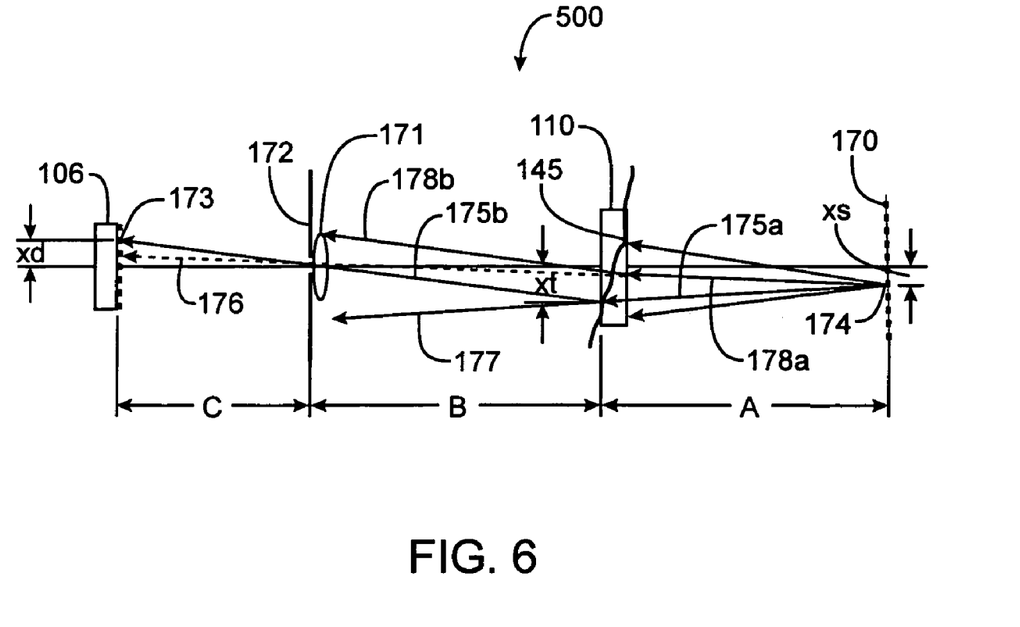
FIG. 6 is a side view of a wavefront sensor device according to another embodiment of the present invention.

Referring now to FIG. 6, in yet another embodiment, a wavefront sensor of the present invention may include a pattern distortion measuring apparatus 500 to provide wavefront gradient measurement. Apparatus 500 uses a light source 170 that provides a luminous pattern, typically but not necessarily an alternating pattern of dark and luminous stripes. Light source 170 is located a known distance A from test surface 110. Light from light source 170 passes through test surface 110 to a lens 171 located at distance B from surface 110. Lens 171 has a small aperture created by a stop 172 so that it acts somewhat like a pinhole camera. An image 173 of light from light source 170 is formed by lens 171 on light sensor device 106. Image 173 is distorted by the presence of ablated test object 110. Consider the rays emanating from location 174, typically the edge between a dark and a luminous part of the source pattern 170 at location xs. In the absence of test surface 110 only dashed ray 176 of all rays from location 174 is able to pass through aperture 172 and reach light sensor device 106. But if test surface 110 is in place, ray 178a is deflected so that a deflected ray 178b does not reach light sensor device, while ray 175a is deflected at a deflection angle 177 so that its deflected ray 175b passes through aperture 172 and strikes light sensor device 106 at location xd. Knowing distances B and C plus measured location xd, the location, xt, on test surface 110 of deflected ray 175b can be found using the geometric principal of similar triangles. Then knowledge of distances A, xt and xs allow the initial direction of travel of ray 175a to be found. Knowledge of distances C and xd allow the final direction of deflected ray 175b after deflection by test surface 110 to be found. The difference between these two ray directions give ray deflection angle 177 caused by ablated test object 110 at location xt to be found. This deflection is the gradient of aberrated wavefront 145 at location xt. When this calculation is done for multiple locations in light source 170, gradients at multiple points on aberrated wavefront 145 may be found, thus providing wavefront gradient information analogous to that found by a Hartmann-Shack sensor system. In practice, if a simple parallel stripe pattern is used, one orientation with the stripes parallel to the vertical axis gives the horizontal component of the gradient. Then the pattern is re-oriented to have the stripes parallel to the horizontal axis and the vertical component of the gradient is found. Crossed grating patterns may be used to find gradient information using only one measurement.

Figure 7A:
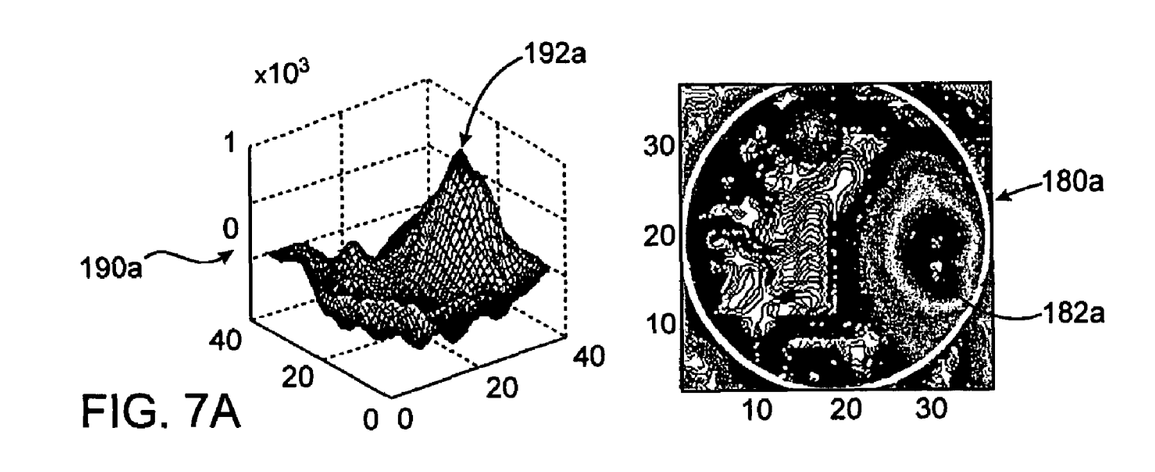
FIGS. 7A-7B are examples of wavefront maps of ablated test surfaces having significant artifacts, the images generated according to principles of the present invention.
Figure 7B:
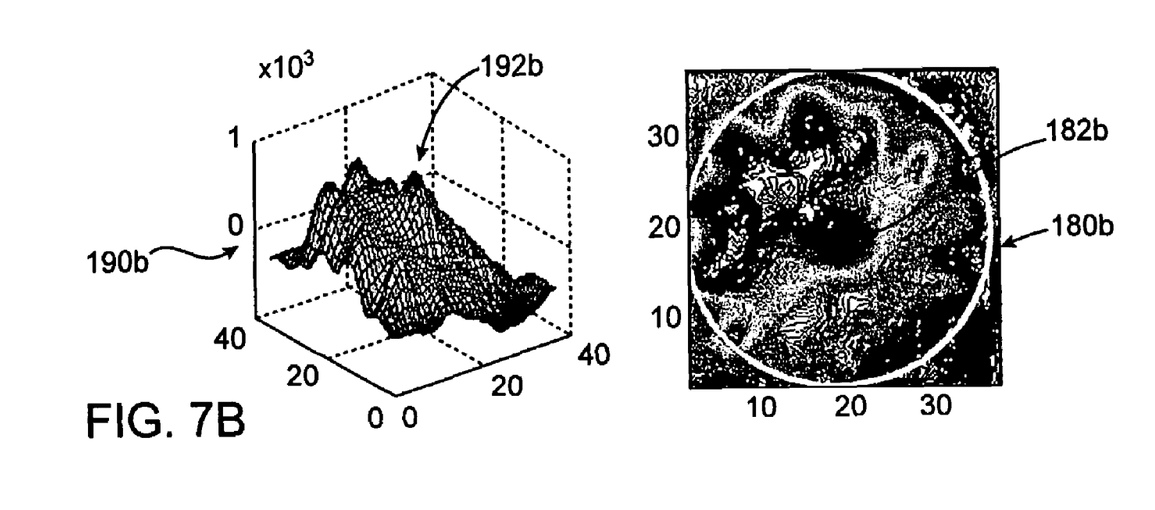

Referring now to FIGS. 7A-7B, one form of data which may be generated by wavefront sensor 100 is one or more surface maps. Surface maps may include, for example, two-dimensional maps 180a, 180b and/or three-dimensional maps 190a, 190b. Surface maps may be helpful in assessing the surface contour or overall shape of test surface 110 and may also be used to derive magnitudes of high-order aberrations and/or artifacts. In some embodiments, for example, high-order aberrations and/or artifacts may be represented by peaks 192a, 192b in three-dimensional maps and/or darker regions 182a, 182b (or lighter regions) on two-dimensional maps. In various embodiments, processor 108 may provide measurements of high-order aberrations and/or artifacts by height, diameter, and/or other dimensions, so that such information can be used for calibration. Typically processor 108 provides surface maps by converting data from light sensor device 106 using a reconstruction algorithm, such as Fourier or Zernike reconstruction algorithms. Any other suitable process used by processor 108 to convert data into a usable form is contemplated, however.

In some embodiments, in addition to providing data regarding high-order aberrations and/or artifacts, wavefront sensor 100 also provides data regarding refractive power of an ablation. Wavefront sensors 100 may further be used to measure wavefront gradients in lenses that have shapes more complex than sphero-cylindrical, such measurements not being possible with current, conventional lensometers.

A variety of refinements, adaptations and modifications are possible within the scope of the present invention. Hence, the scope of the invention is not limited to the specifics of the exemplary embodiments described above but are limited solely by the appended claims.

What is claimed is:

1. A method for analyzing calibration of a laser ablation system for performing an ablation procedure on an eye, the method comprising:

selectively ablating a test surface with the laser system;

directing light from a light source through the test surface; and analyzing the light, after the light has passed through the test surface, to determine a refractive power of the test surface and at least one additional ablation characteristic of the laser ablation system, wherein analyzing comprises measuring wavefront data generated using the light, and using a reconstruction algorithm to generate a surface map of the test surface.

2. A method as in claim 1, wherein the test surface is disposed along a treatment plane, the treatment plane comprising a plane to which a laser is directed from the laser system to perform the ablation procedure, and wherein the light is directed from the light source to the treatment plane through the test surface.

3. A method as in claim 2, wherein the light is analyzed with at least one calibration device.

4. A method as in claim 2, wherein the test surface is fixedly positioned in the treatment plane during ablating, directing and analyzing.

5. A method as in claim 4, further comprising moving the test surface into the treatment plane before the ablating step.

6. A method as in claim 5, wherein moving the test surface comprises moving a platform to which the test surface is coupled.

7. A method as in claim 1, wherein the test surface is ablated into a lens.

8. A method as in claim 1, wherein the test surface comprises a plastic calibration member.

9. A method as in claim 1, wherein selectively ablating comprises applying laser energy to the test surface to approximate at least one procedure selected from a group consisting of astigmatic correction of a human eye, myopic correction of a human eye, hyperopic correction of a human eye, and a phototherapeutic flat.

10. A method as in claim 1, wherein analyzing comprises using at least one wavefront sensor to analyze the light.

11. A method as in claim 10, wherein the wavefront sensor is selected from the group consisting of a Hartmann-Shack sensor, a Tscherning sensor, a ray tracing sensor, a shearing interferometer sensor, an amplitude grating sensor, and a pattern distortion measuring apparatus.

12. A method as in claim 10, wherein analyzing comprises determining at least one of a quality and a shape of the ablated test surface.

13. A method as in claim 12, wherein analyzing the quality of the ablated test surface comprises detecting at least one high-order aberration or artifact on the test surface.

14. A method as in claim 13, wherein analyzing the quality further comprises determining a height of the at least one high-order aberration or artifact on the test surface.

15. A method as in claim 13, further comprising generating at least one map of the test surface, the map showing a location the at least one high-order aberration or artifact on the test surface.

16. A method as in claim 15, the map further showing shapes of the at least one high-order aberration or artifact on the test surface.

17. A method as in claim 1, wherein analyzing comprises:

transforming the light into electrical signals; and processing the electrical signals to determine refractive power and the at least one additional ablation characteristic.

18. A method as in claim 17, further comprising using the electrical signals to generate an image approximately representing the test surface.

19. A method as in claim 1, wherein using the reconstruction algorithm comprises using one of a Zernike reconstruction algorithm and a Fourier reconstruction algorithm.

20. A method as in claim 1, further comprising adjusting the laser ablation system based on the refractive power and the at least one additional ablation characteristic determined during the analyzing step.

21. A method as in claim 20, wherein the at least one ablation characteristic comprises at least one of a quality and a shape of the ablated test surface.

22. A method for analyzing calibration of a laser ablation system for performing an ablation procedure on an eye, the method comprising:

selectively ablating a test surface with the laser system;

directing light from a light source through the test surface; and analyzing the light, after the light has passed through the test surface, to determine a refractive power of the test surface and at least one additional ablation characteristic of the laser ablation system, the light being analyzed by transforming the light into electrical signals, and wherein transforming the light comprises:

allowing the light to pass through a wavefront lens array; and sensing the passed light with a light detection device; and wherein analyzing comprises processing the electrical signals to determine refractive power and the at least one additional ablation characteristic.

23. A method as in claim 22, wherein the light detection device comprises a charge coupled device.

24. A method as in claim 22, further comprising adjusting at least one focusing lens disposed in a path between the test surface and the lens array to adjust the light before it passes through the lens array.

25. A calibration apparatus for use with a laser ablation system, the laser ablation system capable of reshaping a surface by selective laser ablation of the surface, the calibration apparatus comprising:

a selectively laser ablatable test surface;

a light detection assembly, the light detection assembly comprising a wavefront sensor;

a light source for passing light through the ablated test surface, towards the light detection assembly; and a processor coupled with the light detection assembly for analyzing the detected light to determine a refractive power of the test surface and at least one additional ablation characteristic of the laser ablation system, wherein the processor comprises hardware, software, and/or firmware for applying at least one of a Zernike reconstruction algorithm and a Fourier reconstruction algorithm to derive at least one surface map of the test surface from wavefront data measured by the light detection assembly.

26. A calibration apparatus as in claim 25, wherein the test surface is positionable along a treatment plane, the treatment plane comprising a plane to which a laser is directed from the laser system to perform a reshaping procedure, and wherein the light source passes light to the treatment plane, through the ablated test surface, towards the light detection assembly.

27. A calibration apparatus as in claim 26, wherein the test surface is fixedly positioned along the treatment plane while the test surface is ablated and light is passed through the test surface from the light source.

28. A calibration apparatus as in claim 27, further comprising a movable positioning device to which the test surface is coupled, wherein the positioning device is movable to position the test surface along the treatment plane.

29. A calibration apparatus as in claim 28, wherein the at least one positioning device is selected from the group consisting of a movable platform, a jointed arm, a rotating arm, a linear slide and a frame pivot.

30. A calibration apparatus as in claim 25, wherein the ablatable test surface comprises a lens.

31. A calibration apparatus as in claim 25, wherein the ablatable test surface comprises a plastic calibration member.

32. A calibration apparatus as in claim 25, wherein the wavefront sensor is selected from the group consisting of a Hartmann-Shack sensor, a Tscherning sensor, a ray tracing sensor, a shearing interferometer sensor, an amplitude grating sensor, and a pattern distortion measuring apparatus.

33. A calibration apparatus as in claim 25, wherein the light detection assembly comprises a charge coupled device for transforming the light into electrical signals.

34. A calibration apparatus as in claim 33, wherein the processor is coupled with the charge coupled device for analyzing the electrical signals to determine the refractive power and the at least one additional ablation characteristic.

35. A calibration apparatus as in claim 34, wherein the processor is further coupled with the laser ablation system for calibrating the laser ablation system based on the analysis of the electrical signals.

36. A calibration apparatus as in claim 25, wherein the processor comprises means for applying at least one of a Zernike reconstruction algorithm and a Fourier reconstruction algorithm to derive at least one surface map of the test surface from wavefront data measured by the light detection assembly.

37. A calibration apparatus as in claim 25, further comprising at least one adjustment lens disposed between the light source and the light detection assembly for adjusting at least one characteristic of the light.

38. A calibration apparatus as in claim 25, wherein the at least one additional ablation characteristic comprises at least one of a quality and a shape of the ablated test surface.

39. A calibration apparatus as in claim 38, wherein the quality comprises at least one of an high-order aberration and an artifact in the ablated test surface.

40. A calibration apparatus as in claim 39, wherein the processor generates at least one image of the ablated test surface, the at least one image showing the at least one high-order aberration or artifact.

41. A calibration apparatus as in claim 40, wherein the at least one image comprises at least one surface map of the test surface.

42. A calibration apparatus as in claim 39, wherein the processor generates at least one measurement of at least one high-order aberration or artifact.

43. A calibration apparatus as in claim 25, wherein the processor is coupled with the laser ablation system.

44. A calibration apparatus as in claim 43, wherein the processor automatically calibrates the laser ablation system, based on at least one of the refractive power and the at least one additional ablation characteristic.

* * * * *